United States Patent
Demers et al.

(10) Patent No.: US 6,619,288 B2
(45) Date of Patent: Sep. 16, 2003

(54) BREATHING MASK WITH INCOMPLETE HEADBAND

(75) Inventors: Jason A. Demers, Manchester, NH (US); David McGill, Bedford, NH (US); Brian Daniel Tracey, Litchfield, NH (US)

(73) Assignee: Deka Products Limited Partnership, Manchester, NH (US)

(*) Notice: Subject to any disclaimer, the term of this patent is extended or adjusted under 35 U.S.C. 154(b) by 0 days.

(21) Appl. No.: 09/866,888

(22) Filed: May 29, 2001

(65) Prior Publication Data

US 2002/0056457 A1 May 16, 2002

Related U.S. Application Data

(60) Provisional application No. 60/249,064, filed on Nov. 15, 2000.

(51) Int. Cl.$^7$ ............................................. A62B 18/02
(52) U.S. Cl. ........................... 128/205.25; 128/207.13
(58) Field of Search ................ 128/201.19, 201.24, 128/203.13, 203.14, 203.29, 204.11, 205.25, 206.21, 206.27, 206.28, 207.11, 206.18, 207.13; D14/206, 137, 138

(56) References Cited

U.S. PATENT DOCUMENTS

| | | | | | |
|---|---|---|---|---|---|
| 2,792,000 | A | * | 5/1957 | Richardson | 128/201.15 |
| 2,814,293 | A | * | 11/1957 | Gabb et al. | 128/201.19 |
| 3,056,402 | A | * | 10/1962 | Dickinson | 128/206.27 |
| 3,347,229 | A | * | 10/1967 | Heitman | 2128/201.19 |
| 3,683,907 | A | * | 8/1972 | Cotabish | 128/200.28 |
| 3,850,168 | A | * | 11/1974 | Ferguson et al. | 128/201.19 |
| 4,266,540 | A | * | 5/1981 | Panzik et al. | 128/207.13 |
| 4,412,537 | A | * | 11/1983 | Tiger | 128/204.17 |
| 4,491,699 | A | * | 1/1985 | Walker | 379/174 |
| 4,508,936 | A | * | 4/1985 | Ingalls | 128/201.19 |
| 4,537,276 | A | * | 8/1985 | Confer | 128/201.19 |
| 4,641,647 | A | * | 2/1987 | Behan | 128/207.18 |
| 5,048,516 | A | * | 9/1991 | Soderberg | 128/205.25 |
| D340,033 | S | * | 10/1993 | Okumura et al. | D14/192 |
| 5,323,468 | A | | 6/1994 | Bottesch | 381/151 |
| 5,369,857 | A | * | 12/1994 | Sacherman et al. | 29/594 |
| 5,429,126 | A | | 7/1995 | Bracken | 128/207.11 |
| 5,457,751 | A | * | 10/1995 | Such | 381/375 |
| 5,469,505 | A | * | 11/1995 | Gattey et al. | 379/430 |
| D368,716 | S | * | 4/1996 | Shudo | D14/205 |
| 5,697,363 | A | | 12/1997 | Hart | 128/201.24 |
| 5,724,965 | A | | 3/1998 | Handke et al. | 128/207.13 |
| 5,771,886 | A | * | 6/1998 | Maire et al. | 128/201.19 |
| 5,921,239 | A | | 7/1999 | McCall et al. | 128/205.25 |
| 6,065,473 | A | | 5/2000 | McCombs et al. | 128/204.18 |
| 6,247,470 | B1 | * | 6/2001 | Ketchedjian | 128/200.28 |
| D449,289 | S | * | 10/2001 | Weikel et al. | D14/206 |
| D449,376 | S | * | 10/2001 | McDonald et al. | D24/110 |
| D454,554 | S | * | 3/2002 | Gerdom | D14/223 |
| 6,505,623 | B1 | * | 1/2003 | Hansen | 128/207.11 |

FOREIGN PATENT DOCUMENTS

| | | | |
|---|---|---|---|
| DE | 4307754 A1 | 3/1993 | A61M/16/06 |
| GB | 775911 | 5/1957 | |

OTHER PUBLICATIONS

Breeze Sleepgear, http://cpap.net/breeze.htn, p. 1–3, Feb. 19, 2001.
Villeneuve, J–M Int'l Search Report, PCT/US01/43761, Aug. 8, 2002.

* cited by examiner

*Primary Examiner*—Weilun Lo
*Assistant Examiner*—Teena Mitchell
(74) *Attorney, Agent, or Firm*—Bromberg & Sunstein LLP

(57) ABSTRACT

A breathing mask for delivering oxygen to a patient. The breathing mask has a headset for seating about the cranial region of the head of the patient, with a hollow gas delivery arm coupled to the headset. The mask also has a nosepiece that is coupled only to the hollow gas delivery arm and that delivers oxygen to the nostrils of the patient. Finally, the mask has a source of oxygen for coupling oxygen to the hollow gas delivery arm.

11 Claims, 4 Drawing Sheets

BREATHING MASK WITH INCOMPLETE HEADBAND

The present application claims priority from U.S. Provisional Application 60/249,064, filed Nov. 15, 2000, which is herein incorporated by reference.

FIELD OF THE INVENTION

The present invention pertains to masks for supplying oxygen to a subject for breathing.

BACKGROUND OF THE INVENTION

Current oxygen masks employed by individuals suffering from respiratory problems are typically cumbersome and unattractive. It is generally therapeutically indicated that the mask cover the nose or both the nose and the mouth, and that the mask must make a tight seal with the face in order to deliver oxygen to the patient. In many cases, the oxygen must be delivered at a pressure higher than ambient pressure in order to assist the patient in breathing, as, for example, by preventing complete collapse of the lungs. If the mask does not make a tight seal with the face, the oxygen will leak past the mask. As a result, the oxygen delivery rate to the patient is lower.

In certain situations, the orientation of the head of the patient is critical to effective delivery of the oxygen. When a patient with apnea sleeps facing upward, soft tissues such as tonsils and the pharynx can fall back and block the airway. In response, the patient ceases to breathe. As a result, carbon dioxide levels increase until the patient stirs and awakens. Hypoventilation, i.e., breathing that is inadequate to meet the oxygen needs of the body, results not only in restless sleep, but also in increased right side heart forces, in increased pulmonary arterial pressures, and, ultimately, in right side heart failure. Existing masks, however, force a patient to sleep facing upwards.

Breathing masks are typically made of a clear hard plastic such as acrylic, polycarbonate, or PET. To create a tight seal with the face, masks have a rim of flexible polymer, such as silicone. However, pressure is still necessary to press the mask against the face and to deform the flexible polymer in order to form the seal.

Existing breathing masks typically use a strap on each side of the mask connected to a head brace arrangement. The straps are elastic to provide the necessary inward (i.e., toward the face) force to keep the mask seated against the face. In lying against the face of the patient, the straps can become irritating after prolonged use. In addition, the visibility of the straps is a distraction to both patient and others. The advantage of using a strap on each side of the mask is prevention of racking (displacement of the mask to the left or right of the patient) of the mask due to sudden head movement.

Another device known in the art provides a semi-rigid band extending from the back and directly over the top of the patient's cranium and forehead, and over the patient's nose. This configuration may be considered unbecoming and thus socially obtrusive, and may also significantly restrict the field of view of the patient.

Oxygen or oxygen enriched gas or air, collectively referred to herein as oxygen, is provided to a breathing mask through a supply tube. The supply tube is flexible and usually exits from the top of the mask (typically, between the eyes) or from the bottom. Both exits are problematic. When the supply tube enters from the top of the mask, the tube is in the patient's field of view and is very distracting. When the supply tube enters from the bottom of the mask, the supply tube covers the patient's mouth. In either case, the supply tube adds another distracting feature, along with the mask and mask straps, that the patient and others may find unacceptable.

SUMMARY OF THE INVENTION

In accordance with preferred embodiments of the invention, there is provided a headset-type breathing mask for delivering oxygen to a patient. The breathing mask has a headset for seating about the cranial region of the head of the patient, with a hollow gas delivery arm coupled to the headset. The mask also has a nosepiece that is coupled only to the hollow gas delivery arm and that delivers oxygen to the nostrils of the patient. Finally; the mask has a source of oxygen for coupling oxygen to the hollow gas delivery arm.

In accordance with further embodiments of the invention, the hollow gas delivery arm may be pivotally coupled to the headset and may be coupled to the nosepiece by a ball-and-socket coupling. The headset may be seated about the cranium of the patient by means of an ulterior band spanning the top of the head of the patient and a posterior band traversing the back of the head of the patient. The posterior band traversing the back of the head of the patient may have two pads coupled to it for reducing lateral movement of the mask.

In accordance with yet further embodiments of the invention, the breathing mask may also have an electronics assembly for wireless communications, a speaker for through-bone audio transmittal to the patient, and a microphone.

BRIEF DESCRIPTION OF THE DRAWINGS

The invention will be more readily understood by reference to the following description, taken with the accompanying drawings, in which.

DETAILED DESCRIPTION OF SPECIFIC EMBODIMENTS

The present invention advantageously addresses the cited problems with current head-set type nasal masks by eliminating the cosmetic unattractiveness of both the straps and the supply tube and by permitting a patient to rest his head against a surface on the side of his face. The straps that are used in prior art devices to retain a nosepiece against the face are eliminated in accordance with preferred embodiments of the present invention.

Figure 1:
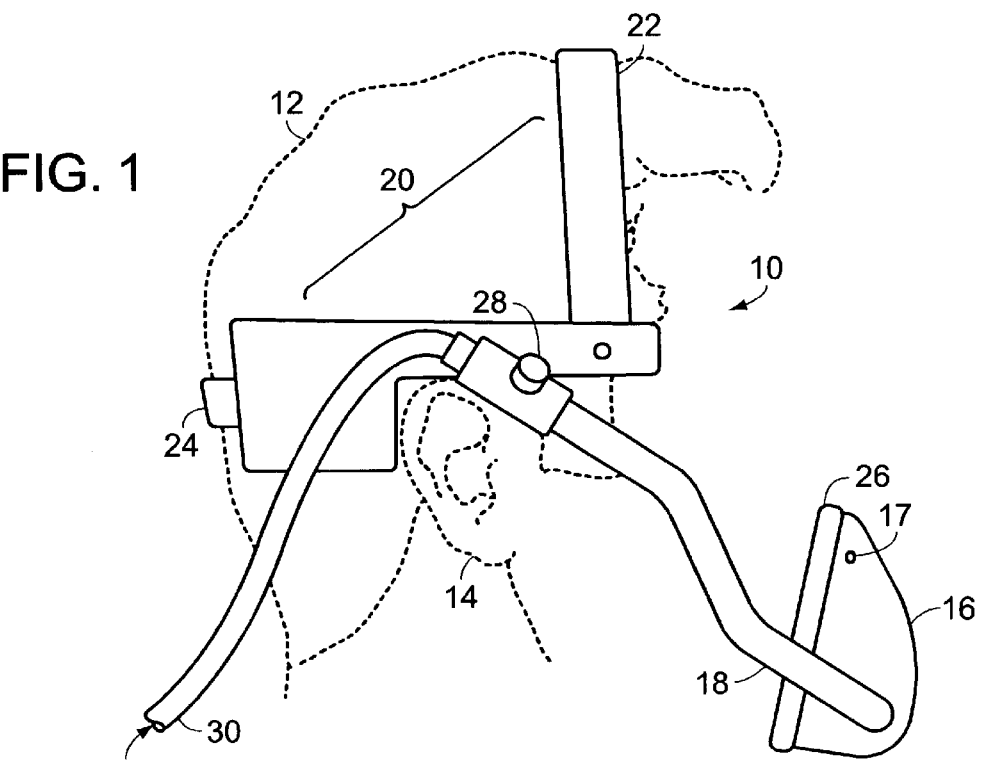
FIG. 1 is a side view of a head-set type breathing mask in accordance with embodiments of the present invention.

Referring first to FIG. 1, a side view is shown of a headset-type breathing mask, designated generally by numeral 10, in accordance with a preferred embodiment of the present invention. Breathing mask 10 serves to deliver gas, typically oxygen, to a patient, whose cranium 12 and ear 14 are designated by dashed lines. In order to allow the patient to breathe the delivered gas, a nosepiece 16 is provided that covers the nose so that only the delivered gas is available for inhalation through the nostrils. Nosepiece 16 is fabricated to conform generally to the contours of the face surrounding the nose, and is typically molded as known in the art. Ventholes 17 are provided in the nosepiece to allow pressure to bleed off at a specified leak rate, in accordance with known practice. Typical materials for the nosepiece include, for example, clear hard plastics such as acrylic, polycarbonate, or PET. In order to create a tight seal, nosepiece 16 is provided with a rim 26 of flexible polymer, for example silicone, that forms a seal with the face.

Whereas, in the prior art, the nosepiece might be retained against the face by means of uncomfortable and unsightly straps, in accordance with preferred embodiments of the present invention, nosepiece 16 is coupled only to a single rigid and hollow delivery arm 18 that supplies the oxygen to the patient.

Figure 2:
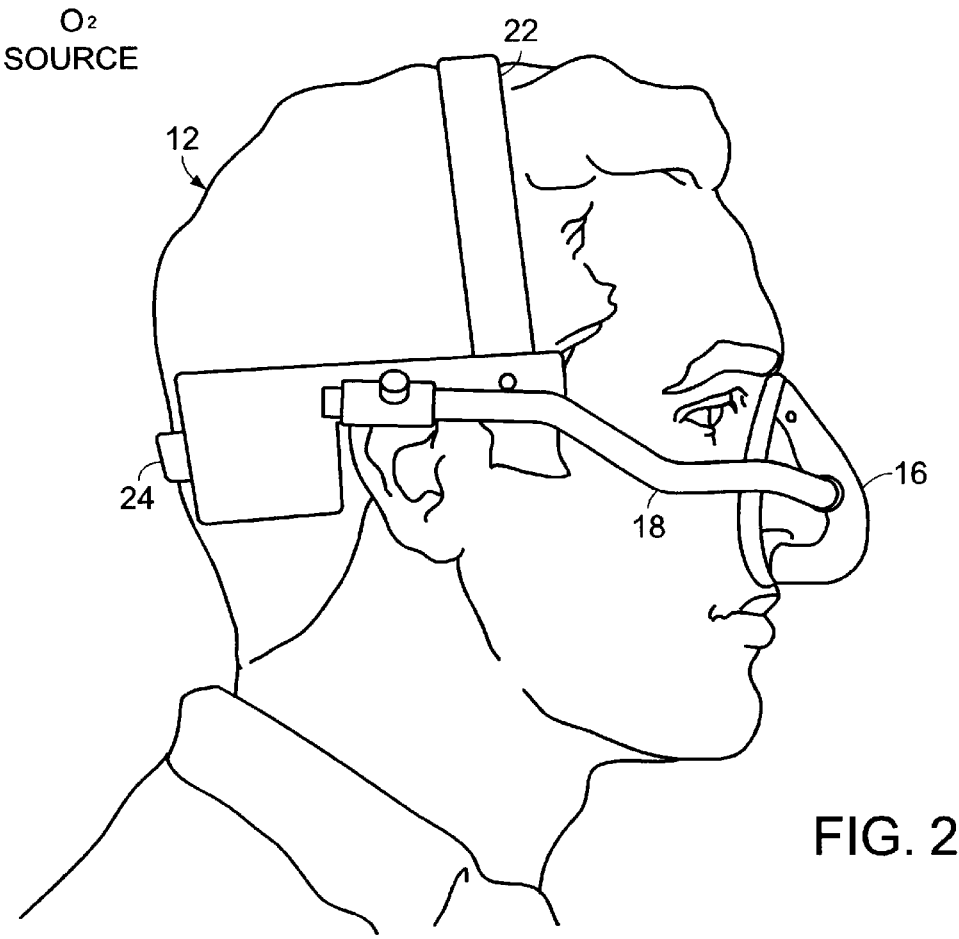
FIG. 2 shows a view of the breathing mask of FIG. 1 disposed on the face of a patient.

Rigid hollow delivery arm 18 is retained with respect to the head of the patient by headset 20. Headset 20, in turn, is secured with respect to the patient's head by means of semi-rigid bands, typically an ulterior band 22 and a posterior band 24. Ulterior band 22 and posterior band 24 respectively span the top and back of the head of the patient, as shown in the side view of FIG. 2. Neither band extends completely around the head. The posterior band terminates well before the ear on the side of the head opposite to rigid hollow delivery arm 18. The ulterior band extends just over the top of the head. The combination of incomplete wrapping of the bands about the head and single hollow delivery arm means that the side of the patient's face opposite to the delivery arm is free of obstruction and available for a patient to use to rest his head as he sleeps.

Referring, again, to FIG. 1, rigid hollow delivery arm 18 provides sufficient inward force (toward the face) on nosepiece 16 to keep the nosepiece sealed against the face of the patient Rigid hollow delivery arm 18 is preferably shaped such that it remains out of the patient's field of view when in use. Rigid hollow delivery arm 18 may be made of a metal such as aluminum or, preferably, of a transparent engineering polymer such as polycarbonate. Adjustment of mask 10 to the facial proportions of the subject patient is provided by the capability of rigid hollow delivery arm 18 to be adjusted about pivot 28 with respect to fixed headset 20. Additionally, delivery arm 18 may be adjusted in a fore/aft direction to provide desired pressure and sealing of nosepiece 16 against the face of the patient.

Figure 7A:
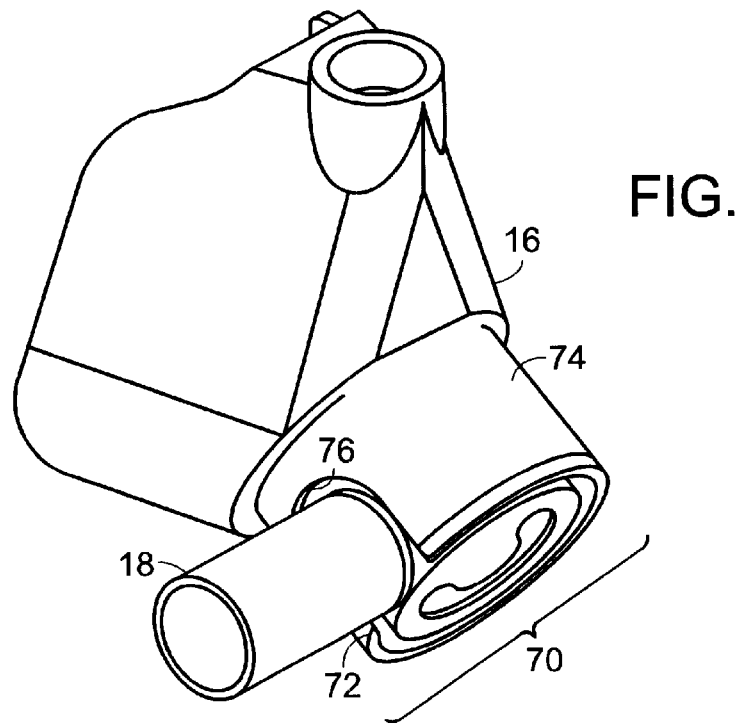
FIGS. 7a and 7b show perspective views, from the side and front respectively, of a ball and socket coupling between the nosepiece and gas delivery arm of the breathing mask of FIG. 1, in accordance with an embodiment of the present invention.
Figure 7B:
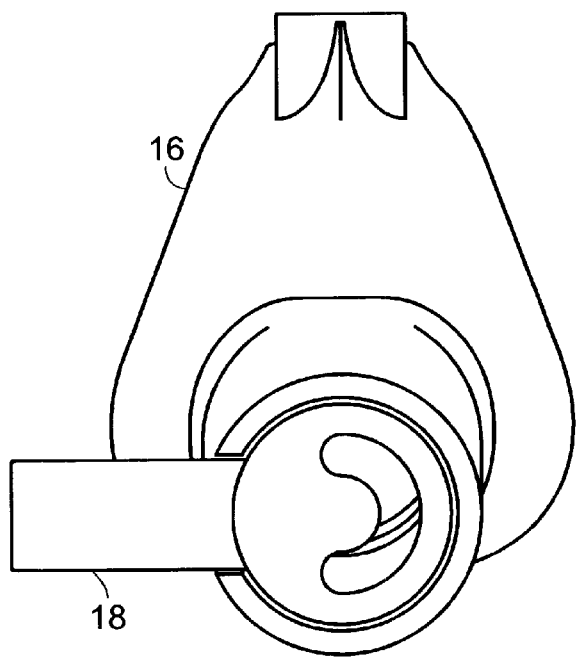

In order to ensure continued inward force of the nosepiece toward the face and to provide comfort for the patient, the coupling between delivery arm 18 and nosepiece 16 may be a ball-and-socket coupling 70 as shown in FIGS. 7a and 7b. FIG. 7a shows a perspective view from the side of coupling 70 showing ball 72 terminating delivery arm 18 and captured by a socket 74 that is molded as part of nosepiece 16 and allows the flow of gas between the delivery arm and the nosepiece. A notch 76 in the periphery socket 74 permits the socket 74 and nosepiece 16 to swivel to a specified degree about the connection to the delivery arm with two axes of rotation, both in the plane of the paper, in the view of FIG. 7b, and in a direction into and out of the plane of the paper.

Referring, once more, to FIG. 1, oxygen is supplied to rigid hollow delivery arm 18 from a standard oxygen supply such as a tank (not shown) that is coupled to the rigid arm via a flexible tube 30.

Figure 3:
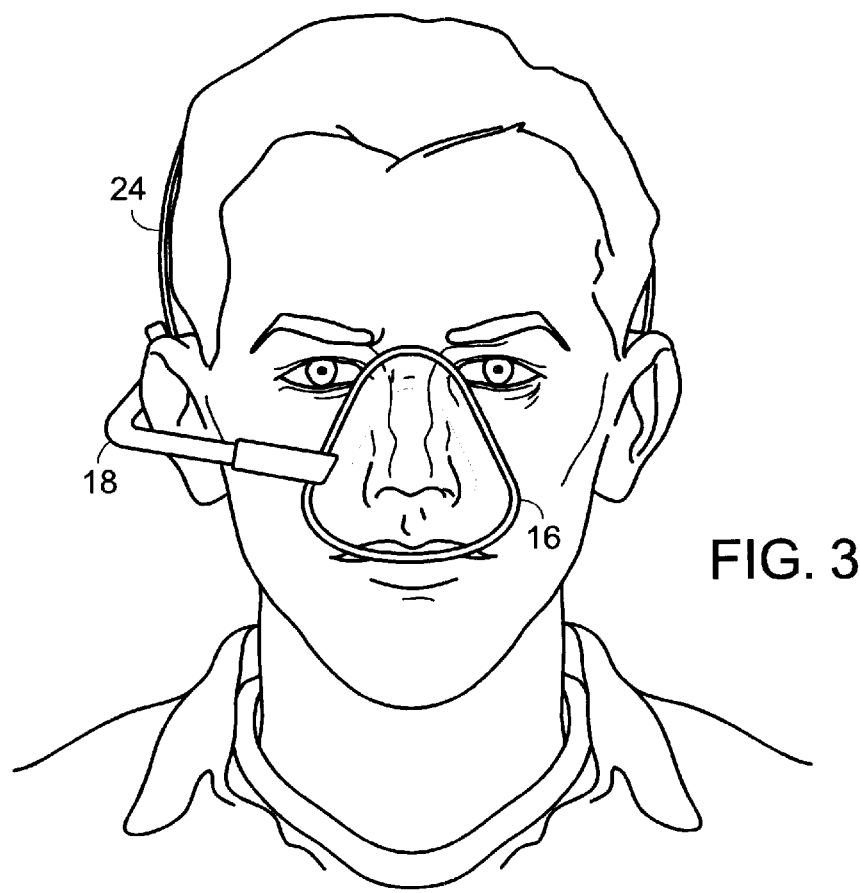
FIG. 3 shows a front view of the breathing mask of FIG. 1 in use on the head of a patient.

A front view of the breathing mask as employed by a subject is shown in FIG. 3.

Figure 4:
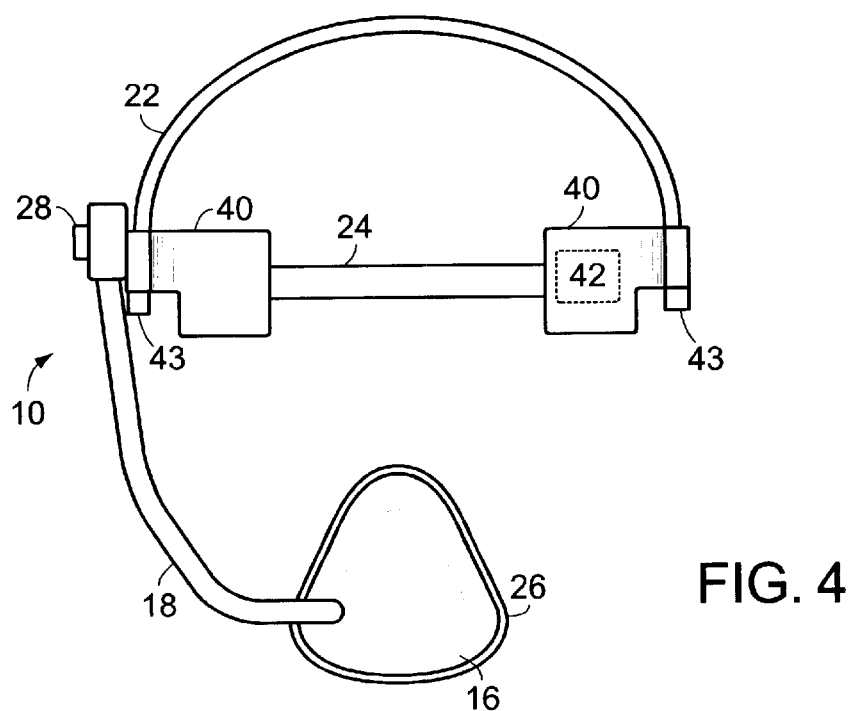
FIG. 4 is a rear view of the breathing mask of FIG. 1.
Figure 5:
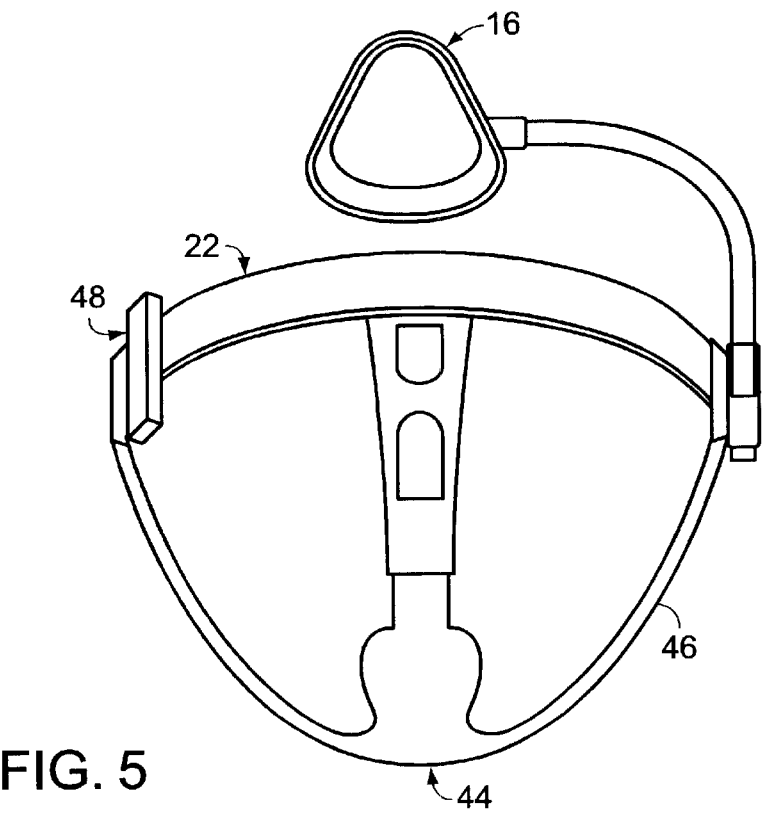
FIG. 5 is a perspective view of a breathing mask showing incomplete ulterior and posterior bands in accordance with another embodiment of the invention.

Referring now to FIG. 4 a rear view is shown of breathing mask 10. The rear view shows two pads 40 on back b d 24 which serve to add comfort to the headset mask and additionally reduce or eliminate racking, which refers to lateral displacement of the mask during sudden head movements. Pads 40 may also enclose electronics 42 to support wireless communications or local computing or speakers 43 for through-bone audio. A perspective view of the breathing mask from the top is shown in FIG. 5. In the embodiment shown in FIG. 5, a back pad 44 and adjustment straps 46 are provided for force dispersion and thus additional stability and comfort. Headband 22 is truncated at one lateral extent 48, here shown as the left side of the patient. These features may advantageously provide greater comfort to a patient reclining on the back or left side.

Figure 6:
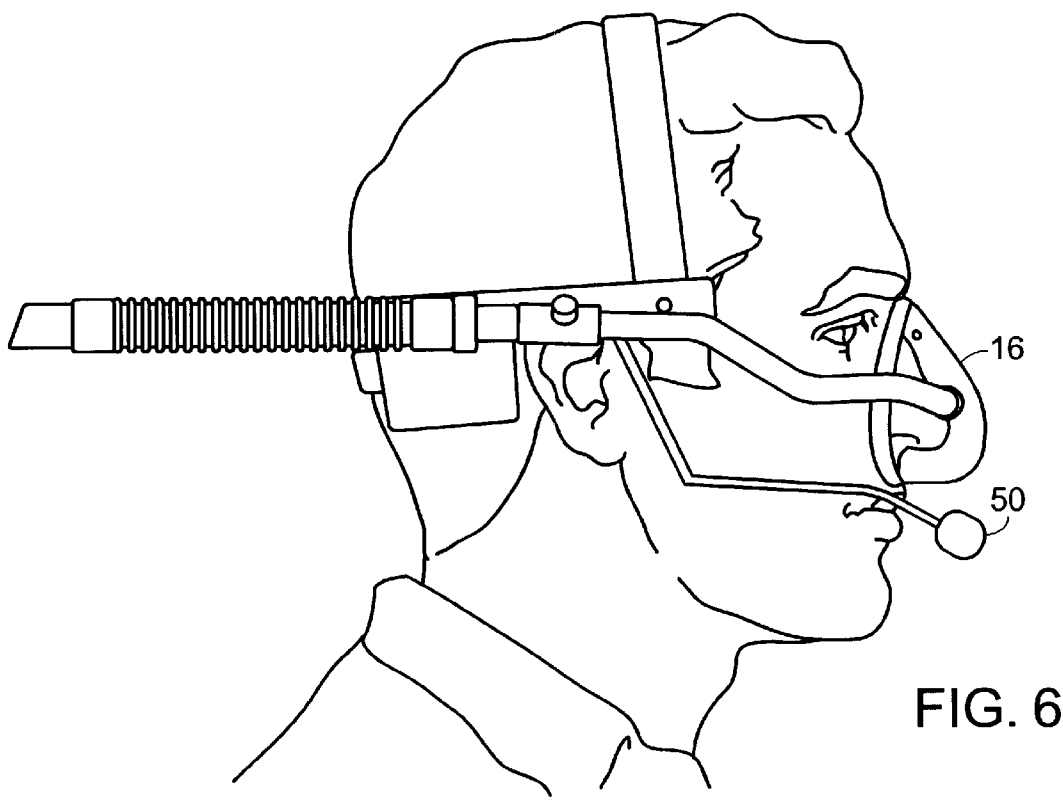
FIG. 6 shows a side view of the breathing mask of FIG. 1 in use on the head of a patient.

In accordance with alternate embodiments of the invention, headset 10 may provide support for microphones placed below the nosepiece and/or earphones. A display may also be mounted on the delivery arm to provide visual information to the patient. FIG. 6 shows an embodiment with a microphone 50 disposed below the nosepiece 16.

Having thus described various illustrative embodiments of the present invention, some of its advantages and optional features, it will be apparent that such embodiments are presented by way of example only and are not by way of limitation. Those skilled in the art could readily devise alternations and improvements on these embodiments, as well as additional embodiments, without departing from the spirit and scope of the invention. All such modifications are within the scope of the invention as claimed.

What is claimed is:

1. A headset-type breathing mask for delivering oxygen to a patient having a face, a nose, and a head, the head having a cranium and cranial region, a top, a bottom, and a back, the breathing mask comprising:
    (a) a headset for seating about the cranial region of the head of the patient;
    (b) a hollow gas delivery arm coupled to the headset;
    (c) a nosepiece coupled only to the hollow gas delivery arm for delivering oxygen to the nose of the patient in such a manner as to substantially seal the nosepiece to the face; and
    (d) a source of oxygen for coupling oxygen to the hollow gas delivery arm.

2. A breathing mask according to claim 1, wherein the hollow gas delivery arm is pivotally coupled to the headset.

3. A breathing mask according to claim 1, wherein the hollow gas delivery arm is coupled to the nosepiece by a ball and socket coupling.

4. A breathing mask according to claim 1, wherein the headset is seated about the cranium of the patient by means of an ulterior band spanning the top of the head of the patient and a posterior band traversing the back of the head of the patient.

5. A breathing mask according to claim 4, further comprising two pads coupled to the back band for reducing lateral movement of the mask.

6. A breathing mask according to claim 1, further comprising an electronics assembly for wireless communications.

7. A breathing mask according to claim 1, further comprising a microphone.

8. A breathing mask according to claim 1, further comprising a speaker for through-bone audio transmittal to the patient.

9. A breathing mask according to claim 1, wherein the headset is seated about the cranium of the patient by means of an ulterior band spanning at least a portion of the top of the head of the patient.

10. A breathing mask according to claim 9, wherein the ulterior band partially spans the top of the head of the patient in such a manner as to allow the head of the patient to rest directly on a surface.

11. A breathing mask according to claim 9, further comprising a posterior band traversing at least a portion of the back of the head of the patient.

* * * * *

UNITED STATES PATENT AND TRADEMARK OFFICE
CERTIFICATE OF CORRECTION

PATENT NO. : 6,619,288 B2
DATED : September 16, 2003
INVENTOR(S) : Jason A. Demers et al.

It is certified that error appears in the above-identified patent and that said Letters Patent is hereby corrected as shown below:

<u>Column 4,</u>
Line 45, replace "a nosepiece coupled" with -- a nosepiece characterized by a periphery and coupled --.
Lines 46-48, replace "patient" with -- patient, wherein the nosepiece contacts the face around the entire periphery in such a manner as to create a substantial seal; and --.

Signed and Sealed this

Fourth Day of May, 2004

JON W. DUDAS
*Acting Director of the United States Patent and Trademark Office*